(12) United States Patent
Wiemker et al.

(10) Patent No.: US 9,483,844 B2
(45) Date of Patent: Nov. 1, 2016

(54) INTERACTIVE IMAGE ANALYSIS

(75) Inventors: Rafael Wiemker, Kisdorf (DE); Thomas Buelow, Grosshansdorf (DE); Sebastian Peter Michael Dries, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 677 days.

(21) Appl. No.: 13/806,301

(22) PCT Filed: Jun. 28, 2011

(86) PCT No.: PCT/IB2011/052834
§ 371 (c)(1),
(2), (4) Date: Dec. 21, 2012

(87) PCT Pub. No.: WO2012/001623
PCT Pub. Date: Jan. 5, 2012

(65) Prior Publication Data
US 2013/0117712 A1 May 9, 2013

(30) Foreign Application Priority Data

Jun. 30, 2010 (EP) .................... 10167830

(51) Int. Cl.
*G06T 7/60* (2006.01)
*G06F 19/00* (2011.01)

(52) U.S. Cl.
CPC .............. *G06T 7/60* (2013.01); *G06F 19/321* (2013.01)

(58) Field of Classification Search
None
See application file for complete search history.

(56) References Cited

U.S. PATENT DOCUMENTS 5,530,759 A 6/1996 Braudaway et al.

| | | |
|---|---|---|
| 7,639,833 B2 | 12/2009 | LeComte et al. |
| 7,742,629 B2 * | 6/2010 | Zarkh .................. G06T 7/0067 345/419 |
| 2006/0274928 A1 | 12/2006 | Collins et al. |
| 2007/0214436 A1 * | 9/2007 | Myers, Jr. ..................... 715/856 |
| 2008/0039707 A1 | 2/2008 | Sato |

(Continued)

FOREIGN PATENT DOCUMENTS

| | | |
|---|---|---|
| JP | 2000-305998 A | 11/2000 |
| JP | 2006-113658 A | 4/2006 |

(Continued)

OTHER PUBLICATIONS

Boulgouris et al, "Segmentation and Content-Based Watermarking for Color Image and Image Region Indexing and Retrieval", EURASIP Journal on Applied Signal Processing, vol. 4, 2002, pp. 420-433.

(Continued)

*Primary Examiner* — Tuan S Nguyen

(57) ABSTRACT

An interactive image analysis system includes an image visualization subsystem (1) for visualizing an image (8). An indicated position determiner (2) is arranged for determining an indicated position of a pointing device with respect to the image(8). A result determiner (3) is arranged for determining a result of a local image processing of the image (8) at the indicated position. A display subsystem (4) displays either at least part of the result of the local image processing (406) or a visible mark (407), based on the image processing result. The result of the local image processing is indicative of the presence or absence of an object (403) at or near the indicated position (404, 405), and the display subsystem (4) is arranged for displaying the visible mark (407) in the absence of such an object (403) at or near the indicated position (405).

6 Claims, 3 Drawing Sheets

(56) References Cited

U.S. PATENT DOCUMENTS

| | | | |
|---|---|---|---|
| 2008/0253737 A1* | 10/2008 | Kimura | G11B 27/005 386/349 |
| 2008/0298634 A1 | 12/2008 | Harada et al. | |
| 2009/0000364 A1 | 1/2009 | Yu | |
| 2009/0047000 A1* | 2/2009 | Walikis et al. | 386/124 |
| 2009/0313555 A1* | 12/2009 | Stovicek et al. | 715/753 |

FOREIGN PATENT DOCUMENTS

| | | |
|---|---|---|
| JP | 2007-298440 A | 11/2007 |
| JP | 2008288726 | 11/2008 |
| JP | 2009060216 A | 3/2009 |

OTHER PUBLICATIONS

Suhail et al, "Security Enhancement for Watermarking Technique Using Content Based Image Segmentation", IEEE, 2007, pp. 772-780.

"Brand Your Slides With a Background Picture, Color, or Watermark", Downloaded From Internet, http://office.microsoft.com/en-US/powerpoint/HA101184961033.aspx?mode=print, Apr. 8, 2010, 6 Pages.

Kankanhalli et al, "Adaptive Visible Watermarking of Images", IEEE, 1999;pp. 568-573.

Kim et al, "A Text Watermarking Algorithm Based on Word Classification and Inter-Word Space Statistics", Proceedings of the Seventh International Conference on Document Analysis and Recognition, IEEE, 2003, 5 Pages.

* cited by examiner

INTERACTIVE IMAGE ANALYSIS

FIELD OF THE INVENTION

The invention relates to interactive image analysis. The invention further relates to display of a visible mark.

BACKGROUND OF THE INVENTION

For web-based medical image processing applications, the transfer of the image data to a server can be a problematic bottle neck, because of the typically large size of medical image datasets. Also to protect the medical data, it may be preferable to leave the image data on the client side, and thus to transfer any application needed for image processing (e.g. a segmentation application) to the client side. However, when the application is transferred to the client, the application could then be easily copied, redistributed, or re-used by a malicious user.

To discourage this, the application can be programmed to display a visible mark, such as a logo, in a corner of the application display window. This visible mark allows the user of the application to know the origin of the software. However, the display of such a visible mark may be removed from the application relatively easily by the malicious user.

SUMMARY OF THE INVENTION

It would be advantageous to have an improved system for interactive image analysis. To better address this concern, in a first aspect, the invention provides a system comprising:
- an image visualization subsystem for visualizing an image;
- a position input for enabling a user to indicate a position with respect to the image, to obtain an indicated position;
- a result determiner for determining a result of a local image processing of the image at the indicated position;
- a decider for deciding whether to display a mark, based on the result of the local image processing, to obtain a decision; and
- a display subsystem arranged for displaying a visible mark in response to the decision.

By making the display of the visible mark dependent on the result of the local image processing, the part of the system responsible for displaying the visible mark becomes more intertwined with the part of the system responsible for determining the result of image processing and/or displaying the result of image processing. This makes it more difficult to tamper with the system in order to avoid the display of the visible mark by the system. The display subsystem may be arranged for displaying either at least part of the result or the visible mark, wherein the selection which one to display is based on the result of the local image processing. Alternatively, the display subsystem may be arranged for switching on and off display of the visible mark, based on the result of the local image processing. The display of at least part of the result does not necessarily need to be suspended during the display of the visible mark.

The result of the local image processing may be indicative of the absence of an object at or near the indicated position. The decider may be arranged for deciding to display the visible mark in the absence of such an object at or near the indicated position. This way, the visible mark is displayed when no information about any object at or near the indicated position is available for display. Consequently, the visible mark does not disturb the interactive analysis of an object by the user.

The result of the local image processing may be indicative of the presence of an object at or near the indicated position. The decider may be arranged for deciding not to display the visible mark, but to display at least part of the result of the local image processing in the presence of such an object at or near the indicated position. This way, the visible mark does not hinder the interactive analysis. For example, when there is an object at or near the indicated position, the display subsystem may be arranged for displaying information about the object. Such information about the object may include dimensions of the object, such as a cross sectional diameter or a volume, and/or a type of the object, and/or an orientation of the object.

The system may comprise an image segmentation unit for performing a segmentation of the image at or near the indicated position, wherein the result of the local image processing is indicative of the absence of an object at or near the indicated position when the segmentation unit fails to segment such an object at or near the indicated position. This way, when the segmentation unit does not find an object, the visible mark can be displayed. When an object is found, the information about the object can be displayed.

The decider may be arranged for deciding to display the visible mark when the result of the local image processing is defined as not meaningful. Consequently, the display subsystem may be arranged for performing the displaying of the visible mark when the result of the local image processing is not meaningful. For example, when a useful result of image processing can only be determined when the image satisfies some predetermined constraints at or near the indicated position, the result of the local image processing is not meaningful when these constraints are not met. Consequently, in such a case the visible mark may be displayed instead of the result of the image processing. This way, the visible mark does not disturb the user during interactive analysis of the image. For example, the result of the local image processing may be considered not meaningful in a flat or noisy region of the image.

The system may comprise a region detector for detecting a region of the image where the result of the image processing is not meaningful. The display subsystem may be arranged for displaying the visible mark in that region. Similarly, in the case where the result of the local image processing is indicative of the presence or absence of an object at or near the indicated position, the region detector may be arranged for detecting a region without objects, and the display subsystem may be arranged for displaying the visible mark in that region. In both cases, the visible mark does not disturb the view of the most interesting portion of the image.

The system may comprise an image processing subsystem for performing the local image processing of the image, based on the indicated position, to obtain the result of the local image processing. This way, the system performs both the image processing and the display of the result. For example, the local image processing may comprise a segmentation of at least part of an object, based on the indicated position.

The display subsystem may be arranged for displaying the visible mark also when the indicated position is outside a display area of the image. Since no result of local image processing is available for positions outside the image, it may be suitable to display the visible mark also when the pointer is outside the portion of the display showing the image.

The visible mark may be indicative of an origin or a right owner with respect to the system. This way, the visible mark helps to identify who has a right with respect to the system. Such a right may comprise a copyright, for example. It helps to prevent and/or discourage counterfeiting. For example, when a malicious user distributes a copy of a software implementation of the system to someone else, the copyright owner of the software implementation is still recognizable by means of the visible mark. For example, the visible mark may comprise a logo, e.g. a company logo. From the logo, the user may assess whether the use of the system is lawful. This way, contents and/or application may be protected. For example, when the system is offered as a web application, and the origin indicated by the visible mark does not correspond to the web site owner, the user will understand that the use of the web application on that web site may be illegal.

In another aspect, the invention provides a workstation comprising the system set forth. The visible mark makes it easy to determine an origin of the system when it is part of the workstation. The workstation may comprise a pointing device for enabling the user to indicate the indicated position, a display for displaying the image, and a communications port for communicating with an image repository and/or a web server. The interactive analysis system may be retrieved by the workstation as a computer program from the web server.

In another aspect, the invention provides an image acquisition apparatus comprising the system set forth. Such image acquisition apparatus may be configured to enable interactive processing of images acquired with the image acquisition apparatus.

In another aspect, the invention provides a method of visualizing a result of local image processing, comprising:
  visualizing an image;
  enabling a user to indicate a position with respect to the image, to obtain an indicated position;
  determining a result of a local image processing of the image at the indicated position;
  deciding whether to display a mark, based on the result of the local image processing, to obtain a decision; and
  displaying a visible mark in response to the decision.

In another aspect, the invention provides a server arranged for transmitting an interactive image analysis application to a client device for execution at the client device, wherein the application is arranged for causing the client device to perform the method of interactive image analysis set forth. Such a server, for example a web server, may enable a user to perform the interactive image analysis by downloading at least part of a software application and running the software application on the client device. Since the software application performs the interactive analysis on the client device, the image data does not have to be transmitted to the server. Moreover, the visible mark protects the software application against being copied and distributed by the user of the client device.

In another aspect of the invention, a method is provided comprising transmitting an application for interactive image analysis to a client device for execution at the client device, wherein the application is arranged for causing the client device to perform the method for interactive image analysis set forth.

In another aspect of the invention, a computer program product is provided comprising instructions for causing a processor system to perform one or more of the methods set forth. Because the display of the visible mark is made dependent on the result of local image processing, the software application code for displaying the visible mark becomes more intertwined with the software application code implementing the local image processing and/or display of the result of the local image processing. This makes it more difficult to remove the visible mark from the application.

It will be appreciated by those skilled in the art that two or more of the above-mentioned embodiments, implementations, and/or aspects of the invention may be combined in any way deemed useful.

Modifications and variations of the image acquisition apparatus, the workstation, the methods, and/or the computer program products, which correspond to the described modifications and variations of the system and server, can be carried out by a person skilled in the art on the basis of the present description.

A person skilled in the art will appreciate that the method may be applied to multi-dimensional image data, e.g. to two-dimensional (2-D), three-dimensional (3-D) or four-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
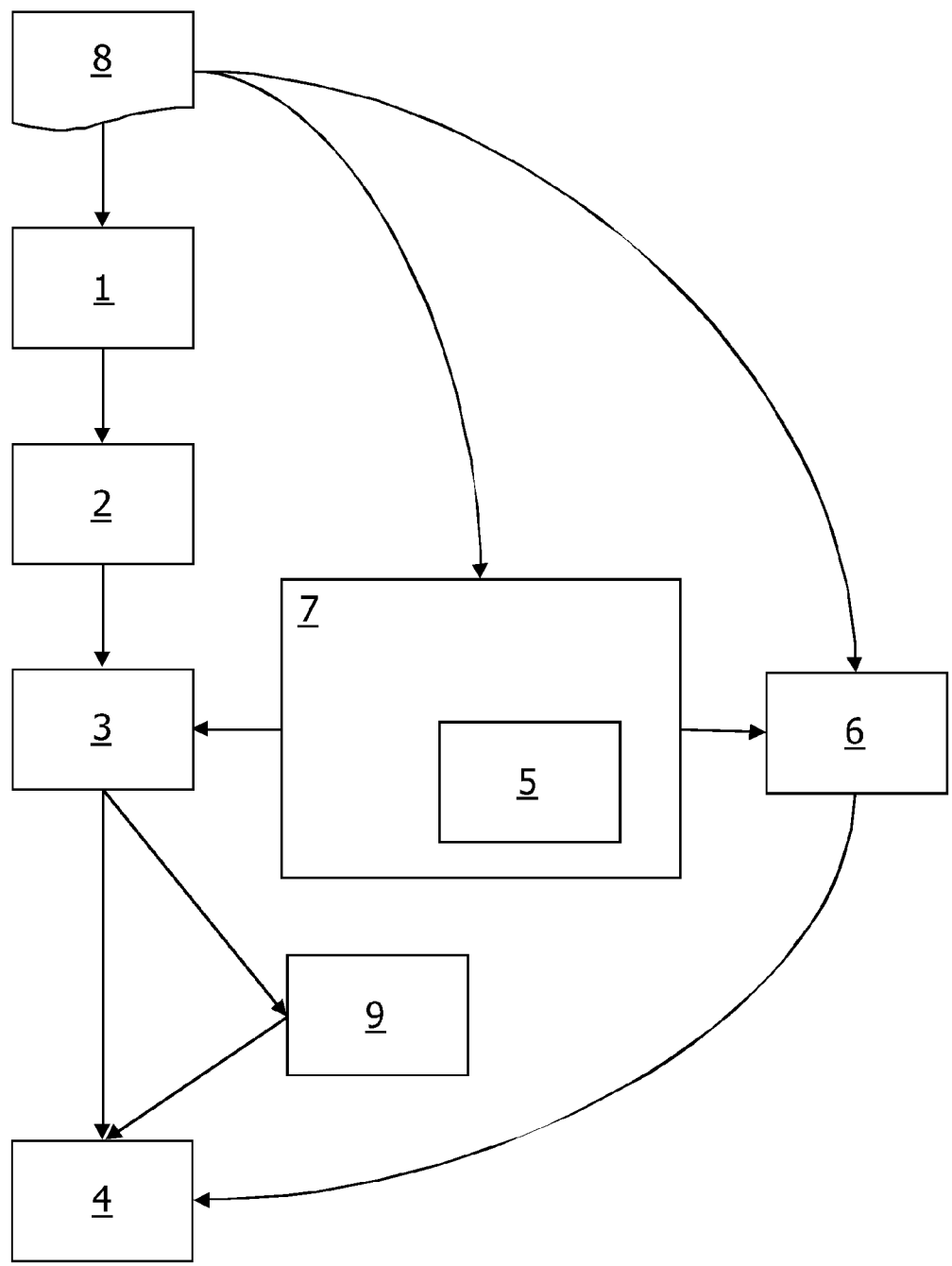
FIG. 1 shows a block diagram of a system for interactive image analysis.

FIG. 1 illustrates aspects of a system for interactive image analysis. The system may comprise an image visualization subsystem 1 for visualizing an image 8. Such an image visualization subsystem is known in the art per se. The image 8 may comprise an image dataset of any type available to the skilled person. The image 8 may comprise, for example, a two-dimensional image or a three-dimensional image. The image visualization subsystem 1 may be configured to generate and display a two-dimensional representation of the three-dimensional image. The system may further comprise a position input 2 configured to enable a user to indicate a position with respect to the image 8, to obtain an indicated position. For example, the position input 2 may be configured to determine an indicated position of a pointing device such as a mouse pointer. The position input 2 may receive coordinates of the pointer with respect to a display area as well as coordinates of the area of the display area on which the image is displayed by the image visualization subsystem 1. By combining these coordinates, a position of the pointer with respect to the image is obtained. The system may comprise a result determiner 3 for determining a result of a local processing of the image 8, e.g. a local image processing, at the indicated position. For example, the result determiner 3 may be arranged for retrieving the result from a storage means containing pre-computed local image processing results. The system may further comprise a display subsystem 4. The display subsystem 4 may be configured to display at least part of the result of the local image processing or a visible mark, in dependence on the result of the local image processing. The display of the visible mark is switched on and off based on the result of the local image processing. The display of the result of the image processing may be switched off during display of the visible mark. However, this is not a limitation.

Figure 4A:
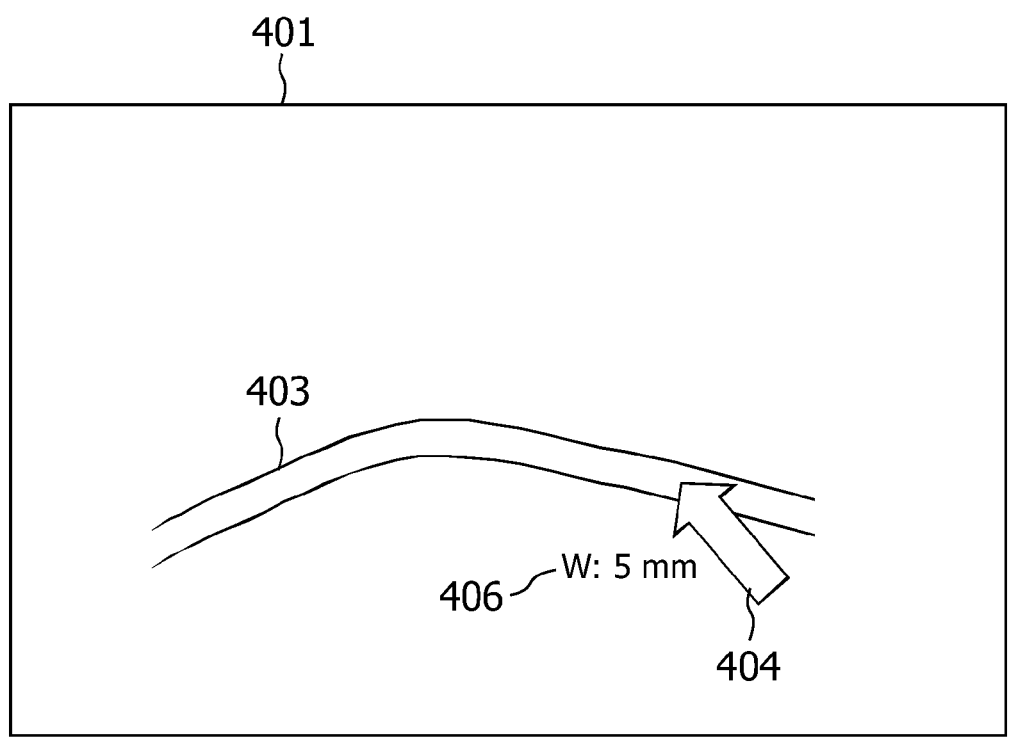
FIGS. 4A and 4B show sketches of screenshots of an application for interactive image analysis.

FIG. 4A shows a sketch of an image area 401 in which the image 8 is displayed. Pointer 404 points at a vessel 403 represented by image 8. The vessel 403 is merely an example of an object which may be represented by image 8. The local image processing in this example comprises locally segmenting the vessel 403 at the position of the pointer 404 and computing the local width of the vessel. The width of the vessel is shown as result 406 of the local image processing.

Figure 4B:
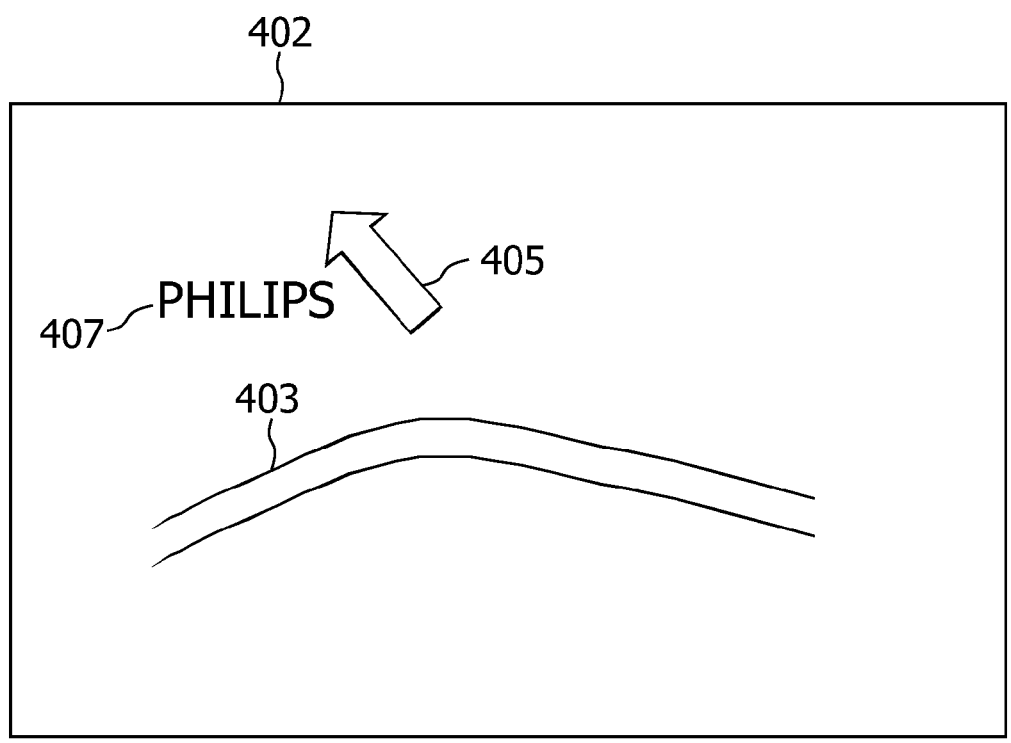

FIG. 4B shows another sketch of the image area 402 in which image 8 is displayed. In the Figures, similar items are indicated by the same reference numerals. In FIG. 4B, pointer 405 points at a position where no vessel 403 is present. Consequently, the image processing does not result in a vessel width, and it is not possible to extract a meaningful vessel width relevant to the position of the pointer 405. In this case, the display subsystem 4 displays the visible mark 407.

In this way, referring in the following to both FIGS. 1 and 4, the result of the local image processing may be indicative of the presence or absence of an object 403 at or near the indicated position 404, 405, and the display subsystem 4 is arranged for displaying the visible mark 407 in the absence of such an object 403 at or near the indicated position 405. To this end, the display subsystem 4 may be controlled by a decider 9 which is arranged for deciding whether to display the visible mark 407 or at least part of the result of the local image processing.

The system may comprise an image processing subsystem 7, and this image processing subsystem 7 may comprise an image segmentation unit 5 for performing a segmentation of the image 8 at or near the indicated position 404, 405. This segmentation unit 5 may be configured to produce a result indicative of the absence of an object 403 at or near the indicated position 405 when the segmentation unit 5 fails to segment such an object 403 at or near the indicated position 405.

The display subsystem 4 may be arranged for performing the displaying of the visible mark 407 when the result of the local image processing is not considered to be meaningful. To determine whether the result of the local image processing is to be considered meaningful, the result determiner 3 may be configured to evaluate whether the result of the local image processing satisfies a set of predetermined conditions. These predetermined conditions may be designed depending on the application. For example, the result of the local image processing may be considered not meaningful in a flat or noisy region of the image. To this end, the result of the local image processing may include a measure of local flatness or noisiness of the image, and the predetermined condition may test whether this measure exceeds a predetermined threshold.

The system may comprise a region detector 6 configured to determine a region of the image where the result of the image processing is not meaningful, and wherein the display subsystem is arranged for displaying the visible mark 407 in this region.

The system may also comprise an image processing subsystem 7 configured to perform the local image processing of the image 8, based on the indicated position 404, 405, to obtain the result of the local image processing. The local image processing may comprise determining e.g. an edginess, or a tissue type based on gray values. When no tissue type is detected for the indicated position (for example when the gray value indicates air), the visible mark may be displayed. The local image processing subsystem 7 may comprise an image segmentation unit 5 for segmenting at least part of an object 403, based on the indicated position 404.

The display subsystem 4 may be configured to display the visible mark 407 also when the indicated position is outside a display area of the image. In such a case, any meaningful local image processing cannot be performed, because the indicated position does not point to an image area.

The visible mark 407 may be indicative of a right owner with respect to the system. The visible mark may also be indicative of an entity which has distributed the system. The visible mark 407 may comprise a logo. The visible mark may be displayed as an overlay over the image, at any location, for example at a fixed location, at a position near the indicated point, or at another location. The visible mark may be translucent, to create a visible watermark, or opaque.

Figure 2:
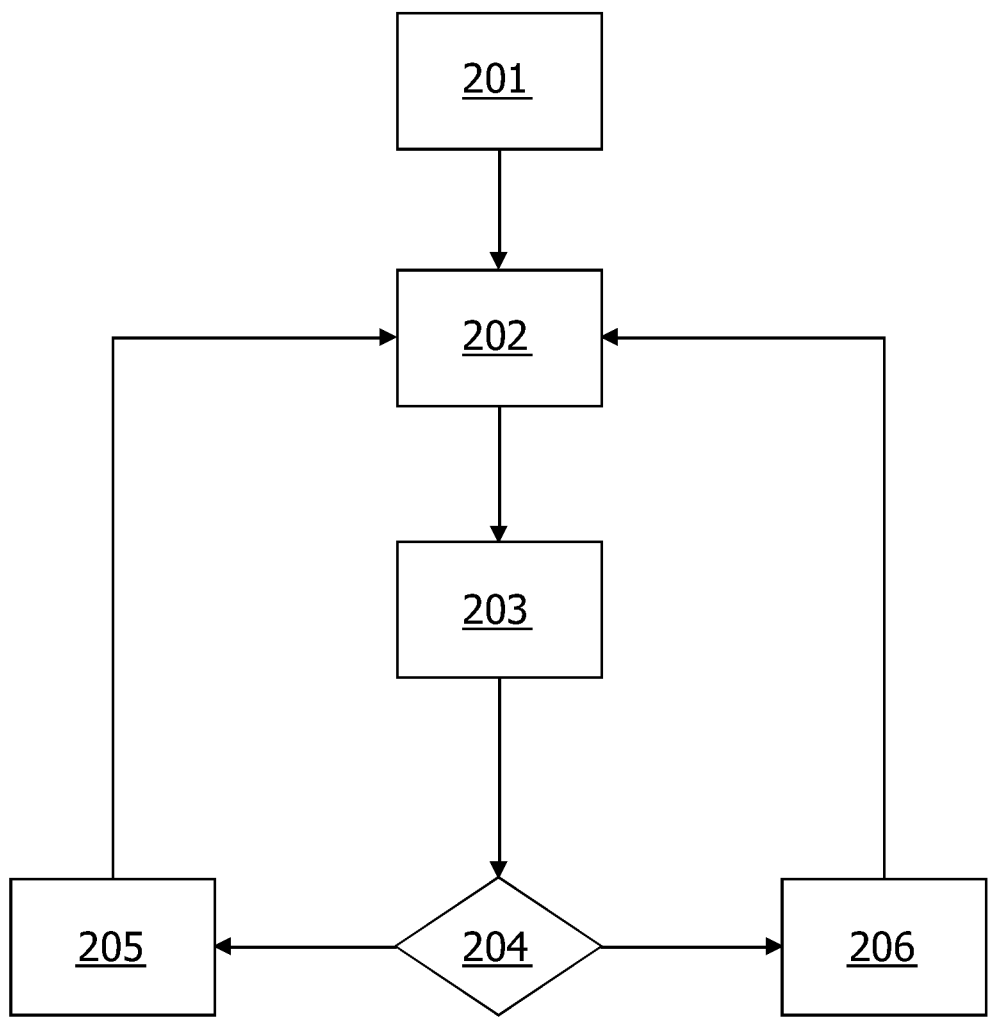
FIG. 2 shows a flowchart of a method of interactive image analysis.

FIG. 2 illustrates aspects of a method of interactive image analysis. The method starts at step 201 of visualizing an image. The method then proceeds with step 202 of receiving an indicated position with respect to the image, for example interactively indicated by a user. Next, in step 203, a result is determined of a local image processing of the image at the indicated position. At step 204, the result of the local image processing is evaluated, which results in a decision as to what to display. Depending on this decision, the method proceeds to step 205 in which at least part of the result of the local image processing is displayed, or to step 206 in which a visible mark indicative of an origin of the interactive system is displayed. After either step 205 or 206, the method returns to step 202 to determine a new indicated position. When no new indicated position is determined in step 202, or when an exit signal is received, the method terminates. The method may be implemented as a computer program product. The method may also be implemented as a web-based application.

Figure 3:
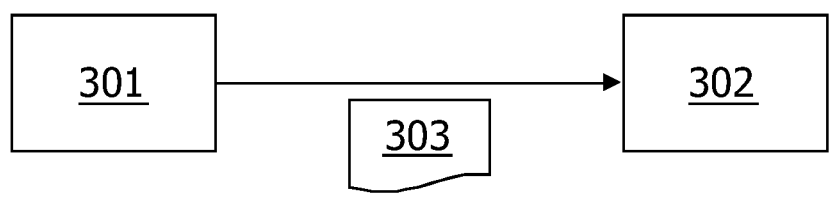
FIG. 3 shows a block diagram of a server arranged for transmitting an interactive image analysis application to a client device.

FIG. 3 shows a block diagram of a client-server system. A server 301 is configured to transmit an interactive image analysis application 303 to a client device 302 for execution at the client device 302. The application 303 is arranged for causing the client device 302 to perform a method similar to the one described in respect to FIG. 2. The server 301 may comprise a web server; the application 303 may comprise a web-based application, such as a JavaScript application, suitable for being executed in a web browser of the client device 302.

Similarly, a method of distributing an interactive image analysis application may be provided. Such a method may comprise transmitting an application 303 for interactive image analysis to a client device 302 for execution at the client device 302, wherein the application 303 is arranged for causing the client device 302 to perform a method similar to the one described in respect to FIG. 2. This method may be implemented as a computer program product.

A web-based live-segmentation algorithm may be devised such that it offers a segmentation result for any image region the mouse pointer points to, but offers a segmentation of a visible mark, for example the shape of the word PHILIPS, when the mouse points to an image region where the segmentation cannot derive a meaningful solution; for example, an image region which is flat or noisy with respect to gray values may not allow a meaningful segmentation. A region comprising air could be such a region. In this way, the web-based segmentation algorithm could still be copied, but its origin would always be obvious by means of the visible mark. The intellectual property may be embedded into the algorithmic behavior in a similar way as a mark is embedded into image data.

The ill-intentioned removal of such an algorithmically intrinsic behavior would be much harder than the removal of e.g. a conventional Philips logo displayed as fixed letters or bitmap.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a floppy disc or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A workstation comprising:
    a display device configured to display a medical diagnostic image;
    a user input device configured to enable a user to indicate a position on the displayed medical diagnostic image;
    a computer configured to:
        receive the indicated position on the medical diagnostic image,
        determine whether a region of the medical diagnostic image at or near the indicated position is medically meaningful based on a predetermined condition to control the display device to display in the region at or near the indicated position:
        (1) a corresponding additional information/data associated with a portion of the medical diagnostic image when the region at or near the indication position is diagnostically meaningful and
        (2) a visible mark indicative of ownership rights when the region at or near the indicated position is determined to be not diagnostically meaningful;
        wherein the predetermined conditions include at least one of noisiness of the region relative to a noisiness threshold, flatness of the region relative to a flatness threshold, presence of edges of tissue in the region, a tissue type in the region based on gray scale values, gray scale values in the region indicative of air, and the indicated position being outside an image display area.

2. The workstation according to claim 1, wherein the computer is further configured to:
    segment the medical diagnostic image; and
    wherein the predetermined conditions include when at least one of a segmented object or a segmentation boundary is in the region of the medical diagnostic image at or near the indicated position.

3. The workstation according to claim 1, wherein the computer is further configured to:
    in response to determining that the region of the medical diagnostic image at or near the indicated position meet the predetermined condition, receiving another indicated position,
    determining whether the region of the medical diagnostic image at or near the another indicated position meets the predetermined conditions,
    based on the determining, controlling the display device to display in the region at or near the another indicated position: (1) a corresponding portion of the medically diagnostic image when the region at or near the another indicated position is diagnostically meaningful and (2) the visible mark indicative of ownership rights when the region at or near the another indicated position is not diagnostically meaningful.

4. A method of interactive image analysis, comprising:

visualizing an image to be interactively analyzed on a display device;

indicating a position with respect to the image with a user input device to obtain an indicated position;

with a computer, determining whether a region of the image at or near the indicated position is meaningful based on a predetermined condition to display (1) a visible mark in the region of the image at or near the indicated position on the display device, wherein the visible mark is indicative of an ownership right with respect to the method, when the region is determined by the computer not to be medically meaningful, and (2) a corresponding additional information/data associated with a region of the image in the region on the display device when the region is determined to be medically meaningful by the computer;

wherein the predetermined conditions include at least one of noisiness of the region relative to a noisiness threshold, flatness of the region relative to a flatness threshold, presence of edges of tissue in the region, a tissue type in the region based on gray scale values, gray scale values in the region indicative of air, and the indicated position being outside an image display area.

5. The method according to claim 4, wherein determining whether the region is meaningful includes comparing properties of the region with predetermined conditions.

6. A non-transitory computer-readable medium carrying software which controls a processor to perform the method according to claim 4.

\* \* \* \* \*